United States Patent [19] [11] 4,043,998

Meares et al. [45] Aug. 23, 1977

[54] 1-(P-BENZENEDIAZONIUM)-ETHYLENEDIAMINE TETRAACETIC ACID

[75] Inventors: Claude F. Meares, Davis, Calif.; Michael W. Sundberg, Penfield, N.Y.

[73] Assignee: The Board of Trustees of the Leland Stanford Junior University, Stanford, Calif.

[21] Appl. No.: 712,534

[22] Filed: Aug. 9, 1976

Related U.S. Application Data

[63] Continuation-in-part of Ser. No. 513,420, Oct. 9, 1974, abandoned.

[51] Int. Cl.[2] ........................ C07C 113/04; C07G 7/00

[52] U.S. Cl. .................................... 260/141; 260/121; 260/501.1; 260/515 P; 260/518 R; 260/562 R; 252/DIG. 11; 424/DIG. 6

[58] Field of Search ....... 260/141 AN, 141 R, 518 R, 260/121; 252/DIG. 11; 424/DIG. 6

[56] References Cited

U.S. PATENT DOCUMENTS 3,809,782 5/1974 Spector ................................ 260/121

FOREIGN PATENT DOCUMENTS 1,221,643 7/1966 Germany ............................ 260/121
828,547 12/1951 Germany ......................... 260/518 R

OTHER PUBLICATIONS

Okaku et al., "Synthesis of Chelating Agents," Bulletin of the Chemical Society of Japan, vol. 40, pp. 2326–2332, (1967).

Yashunskii et al., "Substances With Complex Forming Ability," Chemical Abstracts, vol. 68, p. 10814c, (1960).

Catsch, "Experimental Basis of Therapy With Toxic Radioisotopes," Chemical Abstracts, vol. 50, p. 9599c, (1956).

Rao et al., "Uranium (VI) Complexes With Organic Ligands," Chemical Abstracts, vol. 51, p. 17559b, (1957).

*Primary Examiner*—Daniel E. Wyman
*Assistant Examiner*—John J. Doll

[57] ABSTRACT

1-(p-Benzenediazonium)-ethylenediaminetetraacetic acid is described. This material is a chelating agent which forms stable complexes with the ions of heavy metals including those having radioactive properties and also reacts readily and rapidly with biological molecules. The compound is a versatile reactive agent useful in introducing metal ions into biological molecules.

1 Claim, No Drawings

1-(p-BENZENEDIAZONIUM)-ETHYLENEDIAMINE TETRAACETIC ACID

The invention described herein was made in the course of work under a grant or award from the Department of Health, Education and Welfare.

This application is a continuation-in-part of application Ser. No. 513,420, filed Oct. 9, 1974, now abandoned.

BACKGROUND OF THE INVENTION

Study of biological molecules by combining them with radioactive labels promises to open the way to clearer and more definitive understanding of biological systems. An effective label would be a radioactive metal ion bound by a powerful chelating agent which, in addition to its metal sequestering groups, contains an active functional group which can strongly bond to a biological macromolecule, for instance to a protein. Such labels have not heretofore been available.

GENERAL DESCRIPTION OF THE INVENTION 1-(p-Benzenediazonium)-ethylenediaminetetraacetic acid is a powerful chelating agent and bonds strongly to proteins through its diazonium group. It is useful in that it permits the introduction of metal ions having a variety of useful spectroscopic and radioactive properties into biological macromolecules. 1-(p-Benzenediazonium)-ethylenediaminetetraacetic acid is prepared by preparing 1-phenylglycinonitrile hydrochloride, and then carrying out a series of reactions in which N,N'-Diacetyl-1-phenylethylenediamine, N,N'-Diacetyl-1-(p-nitrophenyl)-ethylenediamine, 1-(p-Nitrophenyl)-ethylenediamine Dihydrochloride, 1-(p-Nitrophenyl)-ethylenediaminetetraacetic acid, 1-(p-Aminophenyl)-ethylenediaminetetraacetic acid and finally 1-(p-Benzenediazonium)-ethylenediaminetetraacetic acid are produced.

DETAILED DESCRIPTION OF THE INVENTION

The chloride sale of 1-(p-Benzenediazonium)-ethylene-diaminetetraacetic acid having the structural formula

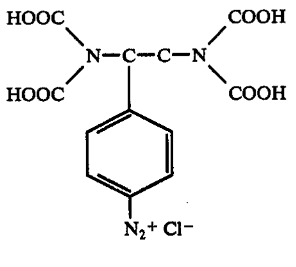

is produced by the following procedure:

Step I — Preparation of 1-phenylglycinonitrile hydrochloride 1-phenylglycinonitrile hydrochloride was prepared from benzaldehyde according to Steiger (Organic Syntheses Col. Vol. III 84(1955) after commercial products proved unsatisfactory. The hydrochloride was precipitated from benzene solution with gaseous HCl. The yield was 30–40%, mp 171°–172°.

Step II — Preparation of N,N'Diacetyl-1-phenylethylenediamine

After treatment with acetic anhydride, 2 g of No. 28 Raney active nickel catalyst (W. R. Grace & Co.) was added to 33 g (0.20 mol) of 1-phenylglycinonitrile Hydrochloride, 25 g (0.30 mol) of sodium acetate, and 250 ml (2.65 mol) of acetic anhydride in a 500 ml Parr bottle. This was placed in a Parr hydrogenation apparatus and agitated at 50° under hydrogen at 45 lb/in$^2$ for 3 hr. Fresh catalyst (1 g) was added, and the reaction was continued for 3 hr, when hydrogen uptake ceased. The mixture was filtered, and the solvent was removed under reduced pressure. The product was extracted from the residue with several portions of boiling ethyl acetate. On reducing the volume and cooling the ethyl acetate solution, 28.8 g (67%) of N,N'-Diacetyl-1-phenylethylenediamine was obtained mp 155°–156°.

Step III — Preparation of N,N'-Diacetyl-1-(p-nitrophenyl)-ethylenediamine 3 g, 0.014 mol of N,N'-Diacetyl-1-phenylethylenediamine was added slowly to 10 ml of 90% $HNO_3$ at −40°. After stirring 5 hr at −40°, the solution was poured over ice and neutralized with $NaHCO_3$. The product was extracted into ethyl acetate, and that was dried with $MgSO_4$ and then evaporated to dryness under reduced pressure. The product was recrystallized from acetone/hexane, yielding 2.2 g (61%) of N,N'-Diacetyl-1-(p-nitrophenyl)-ethylenediamine mp 178°–180°. Anal. ($C_{12}H_{15}N_3O_4$) C, H, N were within 0.4% of theoretical.

Step IV — Preparation of 1-(p-Nitrophenyl)-ethylenediamine Dihydrochloride

A solution of 4 g (0.015 mol) of N,N'-Diacetyl-1-(p-Nitrophenyl)-ethylenediamine in a mixture of 20 ml glacial acetic acid and 30 ml conc. HCl was heated at reflux for 24 hr and then cooled in ice. Upon filtration, 2.5 g (66%) of the crystalline 1-(p-Nitrophenyl)-ethylenediamine Dihydrochloride was collected. Anal. ($C_8H_{13}N_3O_2Cl_2$) C, H, N were within 0.4% of theoretical.

Step V — Preparation of 1-(p-Nitrophenyl)-ethylenediaminetetraacetic acid

A solution of 0.61 g (2.4 mmol) of 1-(p-Nitrophenyl)-ethylenediamine Dihydrochloride and 2.1 g (11.3 mmol) of iodoacetic acid in 10 ml $H_2O$ was held at 45% for 8 hr, with the pH maintained at 10–11 by addition of 7 M KOH. The solution then was acidified to pH 1 with conc. HCl and kept at 4° for 4 days. The crude crystalline product was collected and dissolved in a minimum volume of aqueous NaOH. This was applied to a 3 × 30 cm anion exchange column (Bio-Rad AG 1 × 8 anion-exchange resin in the formate form) and eluted with a linear (0→5 M) gradient of formic acid. The absorbance of the effluent was monitored at 280 nm; elution required 2–3 l. of eluent. The pure tetraacid crystallized in the fraction-collector tubes. In alkaline $D_2O$, the aromatic region of the 60 MHz nmr spectrum of the 1-(p-Nitrophenyl)ethylene-diaminetetraacetic acid product consisted of two doublets, 7.3 ppm and 8.2 ppm downfield from $Me_4Si$. Yield 300 mg (30%), mp 171°–174°. Anal. ($C_{16}H_{19}N_3O_{10}.H_2O$) C, H, N were within 0.4% of theoretical.

Step VI — Preparation of 1-(p-Aminophenyl)-ethylenediaminetetraacetic acid 43 mg, 0.10 mmol of 1-(p-Nitrophenyl)-ethylenediaminetetraacetic acid was dissolved in 50 ml of aqueous NaOH (such that the final pH was 9), and 29 mg of 10% Pd/charcoal catalyst was added. The mixture was stirred gently for 5 hr in an ice bath under 1 atm of hydrogen. The catalyst was removed by filtration, and the filtrate was evaporated to dryness. In $D_2O$, the aromatic region of the 60 MHz nmr spectrum of the 1-(p-Aminophenyl)-ethylenediaminetetraacetic acid product consisted of an aa'bb' pattern centered 7.0 ppm downfield from $Me_4Si$. The differences in the nmr spectra of the products of Steps V and VI make it convenient to monitor the progress of the reduction by nmr. By this criterion, the reduction was quantitative. The product was stored in the dark at −15°.

Step VII — Preparation of 1-(p-Benzenediazonium)-ethylenediaminetetraacetic acid 1-(p-Aminophenyl)-ethylenediaminetetraacetic acid (approx. 0.1 mmol) was dissolved in 0.5 ml $H_2O$; 0.5 ml of conc. HCl was added and the mixture was cooled to 0° in an ice bath. Cold 0.5 M $NaNO_2$ (0.25 ml, 0.125 mmol) was added dropwise with stirring, and the reaction mixture was stirred 1 hr at 0°. Urea (3 mg, 0.05 mmol) was added to destroy excess $NaNO_2$, and the reaction mixture was diluted to 10 ml with cold $H_2O$ to form an aqueous solution of 1-(p-Benzenediazonium)-ethylenediaminetetraacetic acid which was stable for months at −80 °. This solution was standardized by coupling to resorcinol. This step VII of the preparation procedure is a classical diazotization reaction. Hydrochloric acid was used in the reaction and the aqueous solution produced contains the diazonium ion and chloride ion. This step may be carried out using strong acids other than hydrochloric acid such as sulfuric acid, fluoboric acid, phosphoric acid, hydrobromic acid, hydrofluoric acid, trichloroacetic acid and the like to form salts of 1-(p-benzenediazonium)-ethylenediamine tetraacetic acid other than the chloride.

Conjugation of 1-(p-Benzenediazonium)-ethylenediamine-tetraacetic acid with human serum albumin or bovine fibrinogen was accomplished by stirring overnight at 4° C. with a 1% protein solution in 0.01 M EDTA/0.12 M $NaHCO_3$, pH 8.1. Appropriate amounts of 1-(p-Benzenediazonium)-ethylenediaminetetraacetic acid stock solution were neutralized with solid $NaHCO_3$ before addition to the protein solutions. Albumin was reacted with an equimolar amount of 1-(p-Benzenediazonium)-ethylenediaminetetraacetic acid while fibrinogen was reacted with a 2- to 3-fold excess of it. The conjugation may be effected after chelation of a heavy metal ion by the 1-(p-Benzenediazonium)-ethylenediaminetetraacetic acid or the conjugation may be first effected and the conjugation product used to chelate the heavy metal ions.

The ions of Co, Ni, Sn, Cr, Fe, Zr, Hf, Y, Al, In, Ga, Bi, Hg, Rh, Pd, Ir, Os, Ru, Th, U, Tc including ions of their radioactive isotopes and ions of the lanthanides and actinides including ions of their radioactive isotopes form chelates with 1-(p-Benzenediazonium)-ethylenediaminetetraacetic acid or with the azoprotein product obtained by conjugating it with proteins. These chelates are characterized by kinetic inertness and large conditional stability constants and so are suitable materials for use in the investigation and definition of biological systems.

We claim:

1. Salts of 1-(p-Benzenediazonium)-ethylenediaminetetraacetic acid in which the anion is the anion of a strong acid.

* * * * *